(12) United States Patent
Collins et al.

(10) Patent No.: US 11,754,583 B2
(45) Date of Patent: Sep. 12, 2023

(54) METHODS AND APPARATUSES FOR GENERATING TRACE VAPORS

(71) Applicant: GOVERNMENT OF THE UNITED STATES OF AMERICA, AS REPRESENTED BY THE SECRETARY OF THE NAVY, Arlington, VA (US)

(72) Inventors: Greg Collins, Huntingtown, MD (US); Susan Rose-Pehrsson, Fairfax Station, VA (US); Michael Malito, Washington, DC (US); Braden C. Giordano, Reston, VA (US); Adam L. Lubrano, Alexandria, VA (US); Mark H. Hammond, Alexandria, VA (US); Cy Tamanaha, Springfield, VA (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 1104 days.

(21) Appl. No.: 16/276,398

(22) Filed: Feb. 14, 2019

(65) Prior Publication Data

US 2019/0250184 A1    Aug. 15, 2019

Related U.S. Application Data

(60) Provisional application No. 62/630,532, filed on Feb. 14, 2018.

(51) Int. Cl.
*G01N 35/10* (2006.01)
*G01N 33/00* (2006.01)
(Continued)

(52) U.S. Cl.
CPC .......... *G01N 35/1097* (2013.01); *G01N 1/38* (2013.01); *G01N 33/0057* (2013.01);
(Continued)

(58) Field of Classification Search
CPC .. G01N 35/1097; G01N 1/38; G01N 33/0057; G01N 35/1004; G01N 2001/002;
(Continued)

(56) References Cited

U.S. PATENT DOCUMENTS

| 6,834,531 B2* | 12/2004 | Rust | ........................ F27D 11/00 |
|---|---|---|---|
| | | | 95/82 |
| 2016/0077062 A1* | 3/2016 | Leckebusch | ........... G01N 30/06 |
| | | | 73/864.81 |

* cited by examiner

*Primary Examiner* — Robert R Raevis
(74) *Attorney, Agent, or Firm* — US Naval Research Laboratory (57) ABSTRACT

Apparatuses and methods for generating trace vapors are provided. The apparatus includes a controller and an oven. The controller includes: a processor, a memory storing at least one control program, a clean solution supply port constructed to output a clean solution, an analyte solution supply port constructed to output an analyte solution, a carrier gas inlet port constructed to receive a carrier gas, and a plurality of carrier gas supply controllers constructed to output the carrier gas. The oven includes a clean manifold, an analyte manifold, a clean solution nebulizer constructed to: receive the clean solution from the clean solution supply port, and the carrier gas from one of the plurality of carrier gas supply controllers, and output a clean solution vapor stream comprising the clean solution and the carrier gas to the clean manifold, an analyte solution nebulizer constructed to: receive the analyte solution from the analyte solution supply port and the carrier gas from another one of the plurality of carrier gas supply controllers, and output an analyte solution vapor stream comprising the analyte solu- (Continued)

tion and the carrier gas to the analyte manifold, a pneumatic valve controllably connected to the processor and communicatively connected to the clean manifold and the analyte manifold, and an output supply port communicatively connected to the pneumatic valve. The controller is configured to operate the pneumatic valve to allow the clean vapor solution or the analyte vapor solution to enter the chamber and be provided to the output supply port.

13 Claims, 13 Drawing Sheets

(51) Int. Cl.
   *G01N 1/38*    (2006.01)
   *G01N 35/00*   (2006.01)
   *G01N 1/00*    (2006.01)
   *G01N 1/28*    (2006.01)
(52) U.S. Cl.
   CPC ... *G01N 35/1004* (2013.01); *G01N 2001/002* (2013.01); *G01N 2001/2893* (2013.01); *G01N 2035/00277* (2013.01); *G01N 2035/00455* (2013.01)
(58) Field of Classification Search
   CPC . G01N 2001/2893; G01N 2035/00277; G01N 2035/00455
   USPC ....... 422/63, 67, 83; 366/140; 436/179, 181; 73/1.03, 23.2, 23.41, 23.42, 863, 863.01, 73/863.11, 863.33, 864.21, 864.34, 73/864.81
   See application file for complete search history.

METHODS AND APPARATUSES FOR GENERATING TRACE VAPORS

BACKGROUND

Field of the Invention

The present application relates generally to methods and apparatuses for generating trace vapors.

Description of Related Art

Trace vapor detection of explosives and narcotics is critical to protecting the nation from explosive devices and preventing illegal narcotics and cargo from entering the United States. Deployed throughout the United States are sensors designed to detect extremely small concentrations of explosives and narcotics. Each sensor has an operating range over which it can detect concentrations of explosives and narcotics. For example, many sensors can detect concentrations in the parts-per-million range. However, all sensors have a lower limit to their detection ability. For example, a sensor that can detect concentrations in the parts-per-million range may not be able to detect concentrations in the parts-per billion. Research is currently underway to develop new sensors with even more sensitive detection capabilities than those that exist today. However, any such sensors must first be evaluated to ensure they are reliable and accurate. Such evaluations require apparatuses that are capable of reproducibly and accurately generating extremely small concentrations of trace vapor. For certain compounds, that is a difficult task. For example, many narcotics and explosives have compounds with low vapor pressures that make it difficult to accurately produce trace vapor amounts. Currently, techniques such as ink-jet droplet formation or chemical deposition on quartz wool or glass beads placed in temperature controlled zones are used to generate trace vapors. Yet, these techniques have drawbacks. The vapor stream produced by these techniques is either pulsed or steadily declining with time, rather than constant. It can also be difficult to change concentrations for dynamic range studies with these techniques. Finally, none of these techniques offer the capability of switching between clean and analyte air streams. Accordingly, there is a need for a trace vapor generator that is capable of overcoming one or more of these deficiencies.

SUMMARY OF THE INVENTION

One or more the above limitations may be diminished by structures and methods described herein.

In one embodiment, an apparatus for generating trace vapors is provided. The apparatus includes a controller and an oven. The controller includes: a processor, a memory storing at least one control program, a clean solution supply port constructed to output a clean solution, an analyte solution supply port constructed to output an analyte solution, a carrier gas inlet port constructed to receive a carrier gas, and a plurality of carrier gas supply controllers constructed to output the carrier gas. The oven includes a clean manifold, an analyte manifold, a clean solution nebulizer constructed to: receive the clean solution from the clean solution supply port, and the carrier gas from one of the plurality of carrier gas supply controllers, and output a clean solution vapor stream comprising the clean solution and the carrier gas to the clean manifold, an analyte solution nebulizer constructed to: receive the analyte solution from the analyte solution supply port and the carrier gas from another one of the plurality of carrier gas supply controllers, and output an analyte solution vapor stream comprising the analyte solution and the carrier gas to the analyte manifold, a pneumatic actuator controllably connected to the processor and communicatively connected to the clean manifold and the analyte manifold, and an output supply port communicatively connected to a crossover valve. The controller is configured to operate the crossover valve to allow the clean vapor or the analyte vapor to exit the output supply port.

In another embodiment, an apparatus for generating a trace vapor is provided. The apparatus includes an oven, and a first manifold for receiving a first vapor stream comprising an analyte compound. Also included is a second manifold for receiving a second vapor stream comprising a non-analyte compound, an output supply port, an exhaust port, and a valve communicably connected to the output supply port, the first manifold, and the second manifold, and configured to switch between a first state, in which the first vapor stream in the first manifold is permitted to flow to the output supply port and the second vapor stream is permitted to flow to the exhaust port, and a second state, in which the second vapor stream is permitted to flow to the output supply port and the first vapor stream is permitted to flow to the exhaust port. The first manifold and the second manifold are removably disposed in a side of the oven.

In yet another embodiment, a method of generating a trace vapor is provided. A first vapor stream comprising an analyte compound is received into a first manifold. A second vapor streaming comprising a non-analyte compound is received into a second manifold. The first vapor stream or the second vapor stream is provided to an outlet port in accordance with an instruction received from a processor. The first manifold and the second manifold are removably disposed in an oven.

BRIEF DESCRIPTION OF THE DRAWINGS

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

Different Figures may have at least some reference numerals that are the same in order to identify the same components, although a detailed description of each such component may not be provided below with respect to each Figure.

DETAILED DESCRIPTION OF THE PREFERRED EMBODIMENTS

Figure 1:
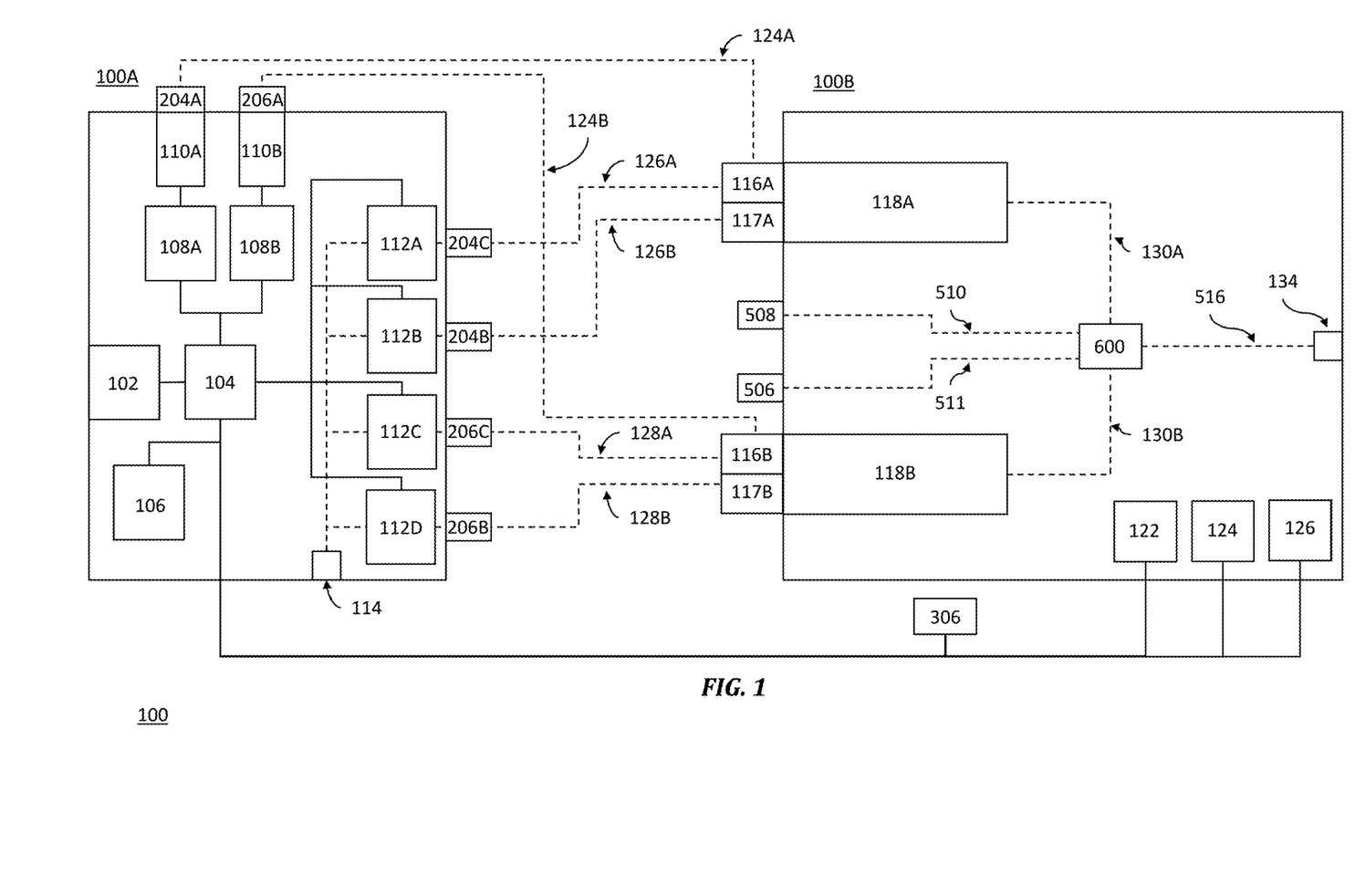
FIG. 1 is a schematic illustration of a trace vapor generator according to one embodiment.

In accordance with example aspects described herein are described methods and apparatuses for generating trace vapors FIG. 1 is a schematic view of a trace vapor generator 100 according to one embodiment. The trace vapor generator 100 is comprised of two units: a controller 100A and an oven 100B. In general, the operation of the trace vapor generator 100 is as follows. Liquids in the form of an analyte solution (that is a compound that will serve as the trace vapor of interest) and a clean solution are provided under the control of controller 100A to oven 100B where they are used to form gaseous vapors with a desired, and accurate, concentration. This process will be described in detail below, beginning with the features shown in FIG. 1.

FIG. 1 is a schematic view of the trace vapor generator 100. As shown in FIG. 1, controller 100A includes a notification unit 102, a processor 104, memory 106, liquid flow controllers (LFC) 108A and 108B respectively corresponding to liquid supply ports 110A and 110B, mass flow controllers (MFC) 112A-112D, and a carrier gas/interferant port 114.

In a preferred embodiment, notification unit 102 is a touch-screen display that not only displays relevant information received from processor 104, but also serves to receive commands from a user and provide the same to processor 104. Processor 104 is communicatively connected to notification unit 102, memory 106, LFCs 108A and 108B, MFCs 112A-112D, as well as elements contained within oven 100B, namely thermocouple 122, blower fan 124, heater 126, and an actuator 306 (as described below). Processor 104 may be embodied as a central processing unit (CPU), microprocessor, or a microcontroller. Memory 106 stores a control program that, when executed by processor 104, provides for overall control of the trace vapor generator 100. Memory 106 also includes storage space for temporary calculations by processor 104 and storing data from previous runs.

As noted above, processor 104 is communicatively connected to LFCs 108A and 108B and MFCs 112A-112D. Processor 104 is constructed to receive instructions for operating LFCs 108A and 108B and MFCs 112-112D. One or more of those instructions may be manually entered by an operator through notification of unit 102 and provided to processor 104 at the beginning of a run of system 100. One or more of those instructions may also be provided in memory 106 and called by processor 104 during the execution of the control program stored in memory 106.

LFCs 108A and 108B control, in accordance with instructions from processor 104, flow of analyte solution and clean solution, respectively. Clean solution contained in a container may be connected to a liquid supply port 110A located on controller 100A. In a preferred embodiment, the clean solution is nearly pure water. Similarly, analyte solution contained in a container may be connected to a liquid supply port 110B. In the exemplary embodiment shown in FIG. 2B, the supply ports 110A and 110B are located in a side of the controller 100A. LFC 108A controls a flow of clean solution 124A from the liquid supply port 110A to nebulizer 116A. LFC 108B controls a flow of analyte solution 124B from the liquid supply port 110B to nebulizer 116B. In one embodiment, LFCs 108A and 108B are a pneumatically modulated liquid delivery systems (PMLDS). Exemplary PMLDS that may be used are described in "Pneumatically Modulated Liquid Delivery System for Nebulizers" NRL/MR/6180-11-9360, Accession Number ADA553750, published Dec. 2, 2011, which is incorporated by reference herein. A PMLDS is a means of delivering delivery a continuous, precisely controlled, pulse-free flow of liquid to a nebulizer. This may be achieved by placing a liquid sample within a sealed container with two pieces of tubing inserted through the cap: one is for liquid delivery to the nebulizer after passage through a liquid flow meter, and the other is for delivery of a modulated pressure to adjust the flow to maintain constant liquid flow. The flow meter provides a feedback to prevent changes in the liquid flow rate with time as the liquid volume in the reservoir vessel decreases. The ability to precisely control the pressure for the liquid flow to the nebulizer using the PMLDS allows for pulse-free, continuous vapor generation limited only by the volume of liquid in the reservoir. In other embodiments, alternate methods of vapor introduction to manifolds 118A and/or 118B may be used including: permeation tubes, gas cylinders, or solid thermal evaporation sources (e.g., TATP).

MFCs 112A-112D control, under the instructions from processor 104, flows of a carrier gas from port 114 to nebulizers 116A and 116B, as well as carrier gas inlets 117A and 117B. More specifically, MFC 112A controls the flow of a carrier gas 126A from port 114 to the nebulizer 116A. MFC 112B controls the flow of the carrier gas 126B from port 114 to carrier gas inlet port 117A. As explained in greater detail below, nebulizer 116A combines the carrier gas from flow 126A with the flow of clean solution 124A to convert the liquid solution to a gaseous vapor at a programmed concentration. The flow of carrier gas 126B is provided to a carrier gas inlet 117A on the oven 100B and used to generate a sheath flow around the nebulizer's 116A vapor flow, as explained below. In a similar manner to MFC 112A, MFC 112C controls the flow of the carrier gas 128A from port 114 to nebulizer 116B. MFC 112D controls the flow of the carrier gas 126B from port 114 to carrier gas inlet port 117B. Similarly to inlet 117A above, the flow of carrier gas 128B provided to carrier gas inlet 117B is used to generate a sheath flow around nebulizer's 116B vapor flow.

Figure 2A:
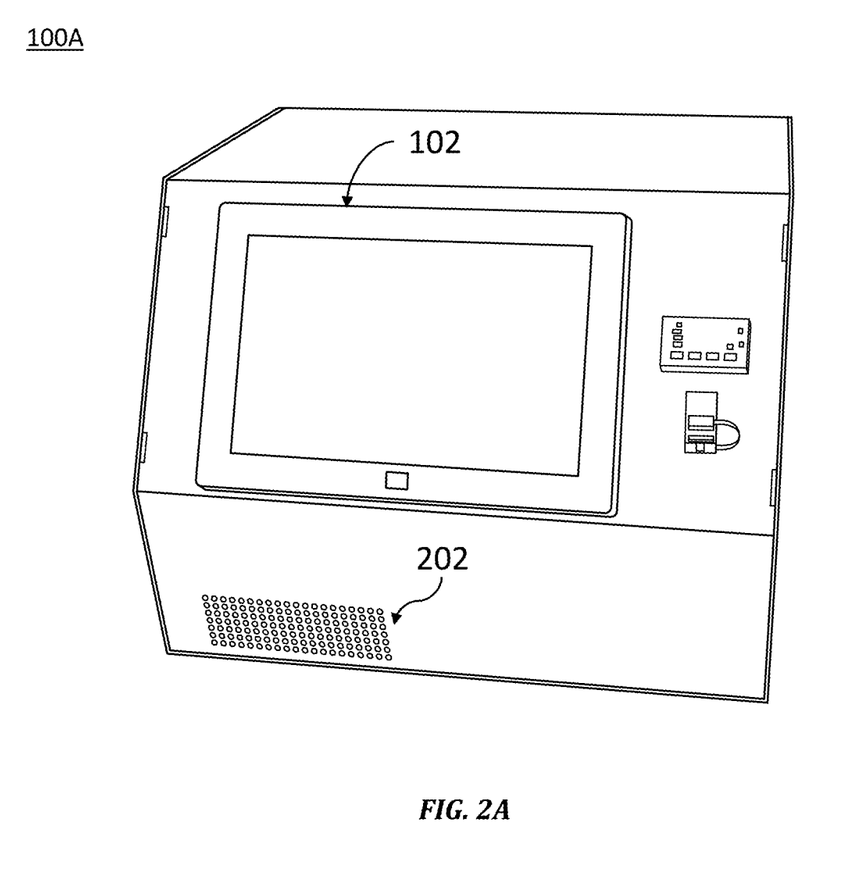
FIG. 2A is a perspective view of a controller of the trace vapor generator according to one embodiment.
Figure 2B:
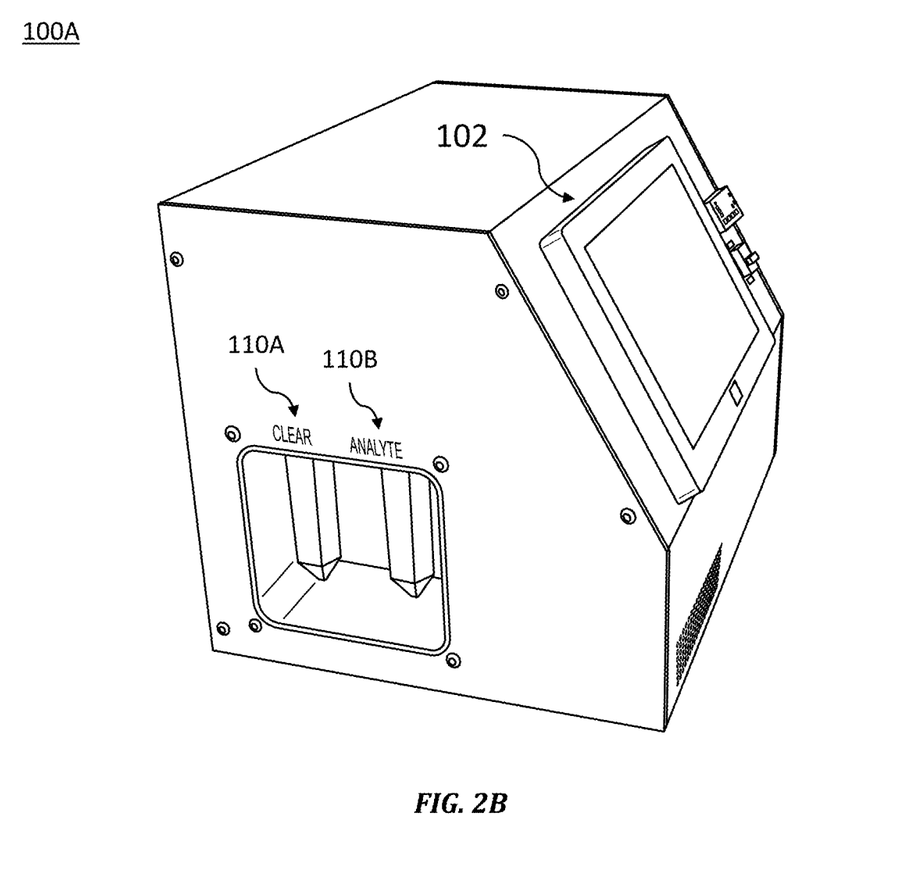
FIG. 2B is another perspective view of a controller of the trace vapor generator according to one embodiment.
Figure 2C:
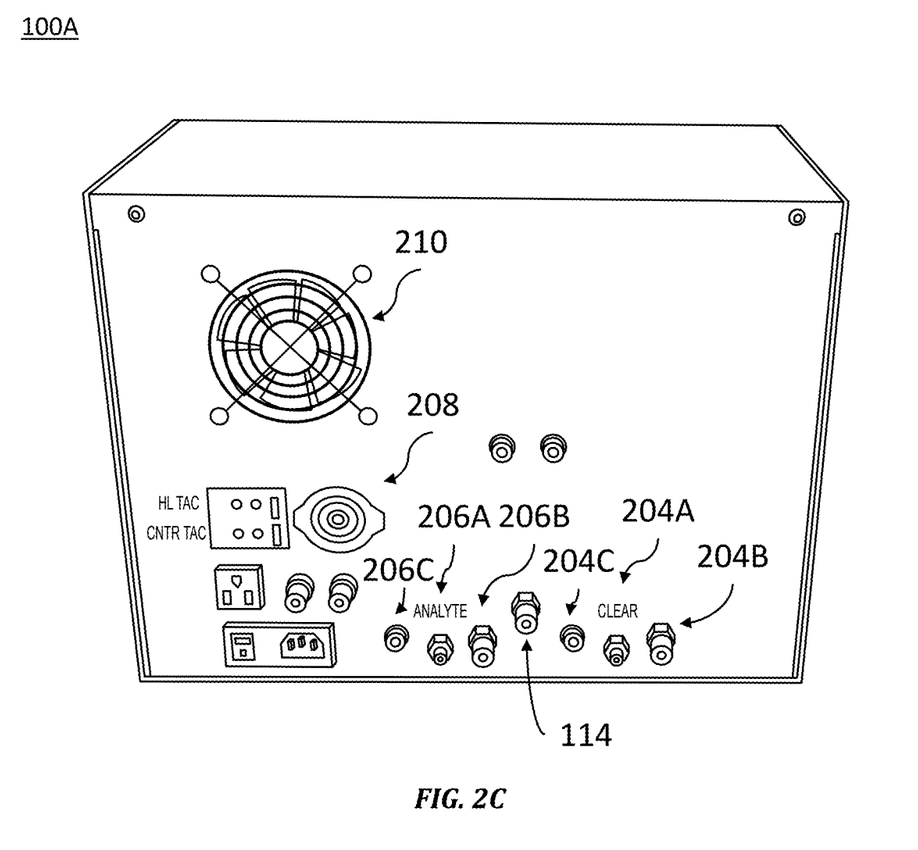
FIG. 2C is yet another perspective view of a controller of the trace vapor generator according to one embodiment.

FIGS. 2A-C are perspective views of the exterior of a controller 100A according to one embodiment. FIG. 2A shows an exemplary touch screen notification unit 102 and a cool air intake port 202 to replace the warm air generated by operation of the controller 100A. FIG. 2B shows the touch screen notification unit 102, and the liquid supply ports 110A and 110B. FIG. 2C shows the rear of controller 100A. As shown in FIG. 2C, the exterior of controller 100A includes connections 204A, 204B and 204C for supplying liquid flow 124A to nebulizer 116A, carrier sheath gas 126B to carrier gas inlet 117A for manifold 118A in oven 100B, and carrier gas 126A to nebulizer 116A, respectively. The exterior of controller 100A also includes connections 206A, 206B and 206C for supplying liquid flow 124B to nebulizer 116B, carrier sheath gas 128B to carrier gas inlet 117B for manifold 118B in oven 100B, and carrier gas 128A to nebulizer 116B, respectively. Also provided on the rear of control 100A are various electrical connections, fuses, and switches for operating controller 100A, along with a cooling fan 210.

Having described the functions of the controller 100A, attention will now be turned to oven 100B. Oven 100B includes, among other features described below, nebulizers 116A and 116B, carrier gas inlets 117A and 117B, manifolds 118A and 118B, a crossover valve 600, a vapor supply port 134, at least one thermocouple 122, a blower fan 124, and a heater 126. The general operation of the oven 100B is as follows. Vapor flows from nebulizers 116A and 116B are combined with sheath flows from the carrier gas provided to inlets 117A and 117B in manifolds 118A and 118B, respectively. The gaseous vapor flows 130A and 130B in the manifolds 118A and 118B, respectively, are provided to a crossover valve 600. Under the control of processor 104, crossover valve 600 controls the path of gaseous vapor flow 130A and 130B. Output flow is then supplied to either tube 510, or both tubes 511 and 516. To prevent adsorption of the gaseous vapors on the surfaces of manifolds 118A and 118B, heater 126 is provided. Heater 126, under the control of processor 104, provides heat to the interior of the oven 100B. The hot air is then circulated by a blower fan 124 to produce an even temperature distribution within the oven 100B. The temperature inside the oven 100B is monitored by a thermocouple 122 which provides temperature readings to processor 104. Based on the temperature readings from thermocouple 122, processor 104 controls the heat output of heater 126.

Figure 3:
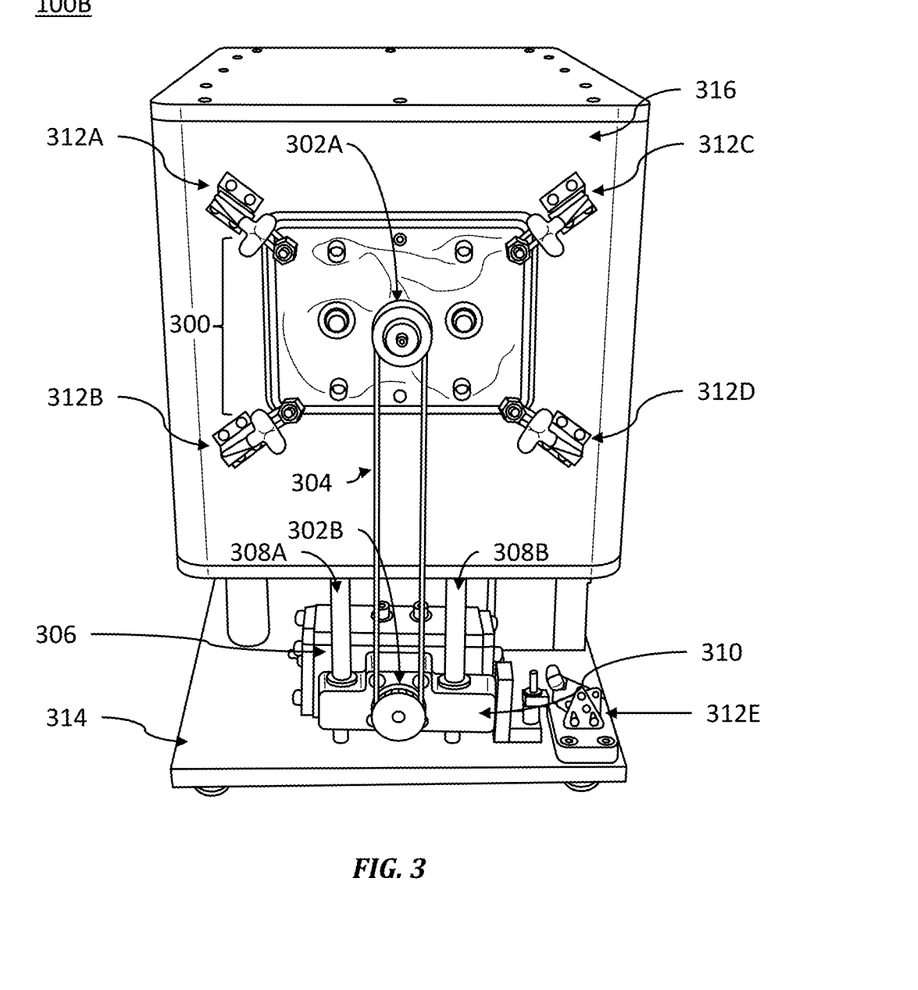
FIG. 3 is a perspective view of an oven of the trace vapor generator according to one embodiment.

FIG. 3 is a perspective view of oven 100B according to one embodiment. As shown in FIG. 3, one end of the oven 100B includes a removable manifold assembly 300. The removable manifold assembly includes a first pulley 302A which is connected to a second pulley 302B by a timing belt 304. Pulley 302B is connected to a pneumatic actuator 306 that operates under the control of processor 104. Processor 104 may activate the pneumatic actuator 306 thereby causing pulley 302B to rotate. That rotation is conveyed by the timing belt 304 and pulley 302A to the crossover valve 600 within oven 100B by a drive shaft 514. Depending upon the amount of rotation of pulley 302B, the crossover valve 600 may be set to allow which input (606A-B)-output (606C-D) pairs to connect as described below. The pneumatic actuator 306 is movably disposed on linear rails 308A and 308B. In the embodiment shown in FIG. 3, actuator 306 is connected to breadboard 314 by a toggle clamp 312E. By releasing toggle clamp 312E, actuator 306 is free to move vertically along linear rails 308A and 308B. By moving actuator 306 towards oven 100B, the tension on timing belt 304 is relieved, thereby allowing the removable manifold assembly 300 to be removed from oven 100B by releasing toggle clamps 312A-312D. Of course, the configuration shown in FIG. 3 is merely one exemplary embodiment, and other means of connecting the components shown therein may be used. For example, as described below, toggle clamps 312A-D may be replaced by thumbscrews.

Figure 4:
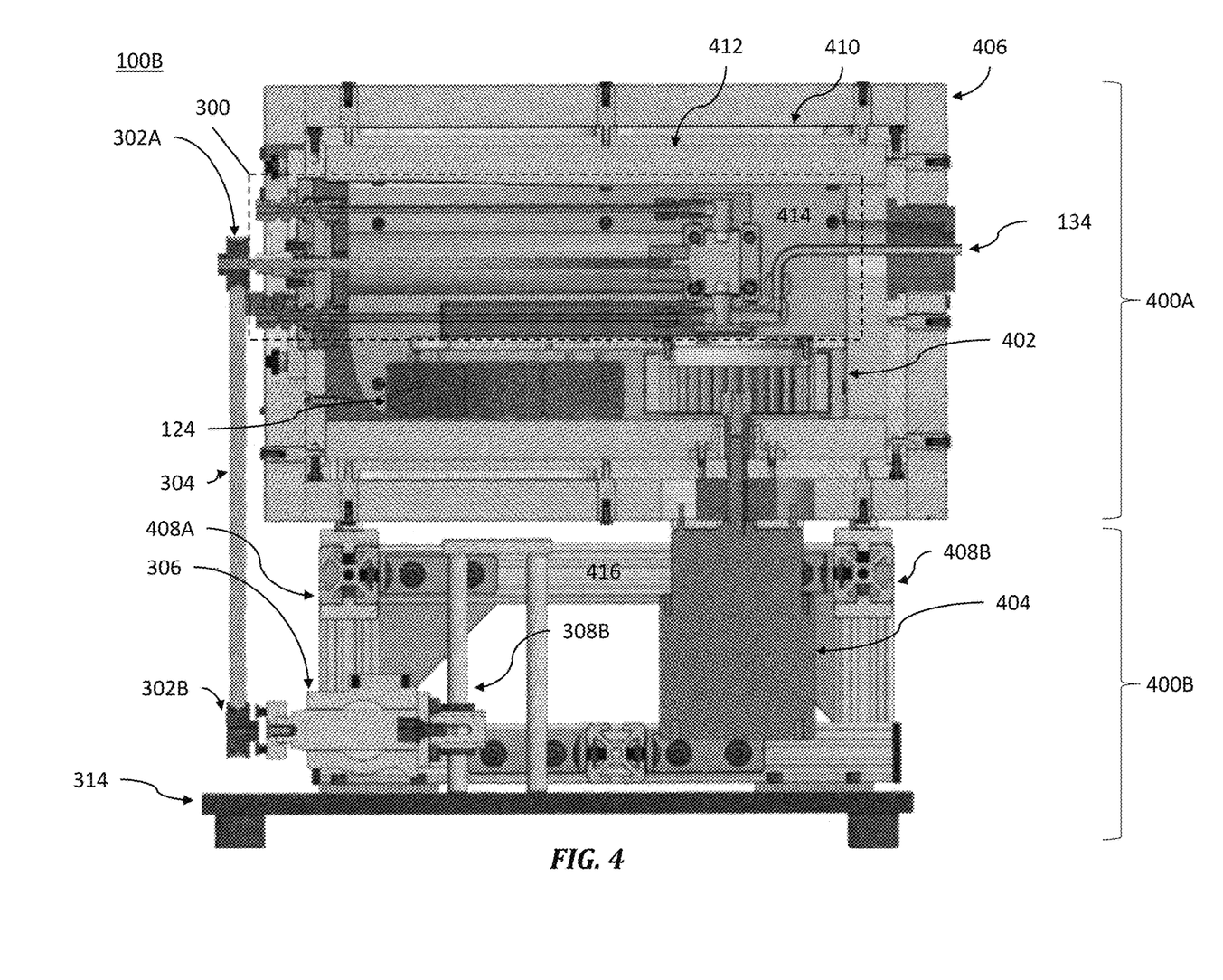
FIG. 4 is a cross-sectional view of the oven of the trace vapor generator according to one embodiment.

FIG. 4 is a cross-sectional view of oven 100B according to one embodiment. As shown in FIG. 4, oven 100B can be further divided into an upper section 400A and a lower section 400B. The upper section 400A includes a frame comprising three layers: an outer ceramic layer 406, an inner ceramic layer 412, and an aluminum frame 410 disposed between the inner and outer ceramic layers 406 and 412. The outer ceramic layer 406 may also include stainless steel sheeting 316 on a periphery thereof, as shown in FIG. 3. By providing two ceramic layers 406 and 412, the overall insulation of the oven 100B is improved which reduces the output requirements of heater 124. The interior of the inner ceramic layer 412 defines an interior of the oven 414. Within the interior of the oven 414 the removable manifold assembly 300 is disposed, along with heater 124 and blower fan 402. Blower fan 402 is rotationally connected to a motor 404 through the frame of the upper section 400A. In a preferred embodiment, motor 404 is a ⅛ horsepower shade pole motor. The lower section 400B includes a frame 416 that includes two support pillars 408A and 408B that connect frame 416 to the aluminum frame 410 of the upper section 400A. Motor 404 and linear rails 408A and 408B are also connected to frame 416. Finally, frame 416 is connected to breadboard 314. Having described the features of oven 100B, attention will now be directed to the removable manifold assembly 300, as shown in FIGS. 5, 6A, 6B, 7A and 7B.

Figure 5:
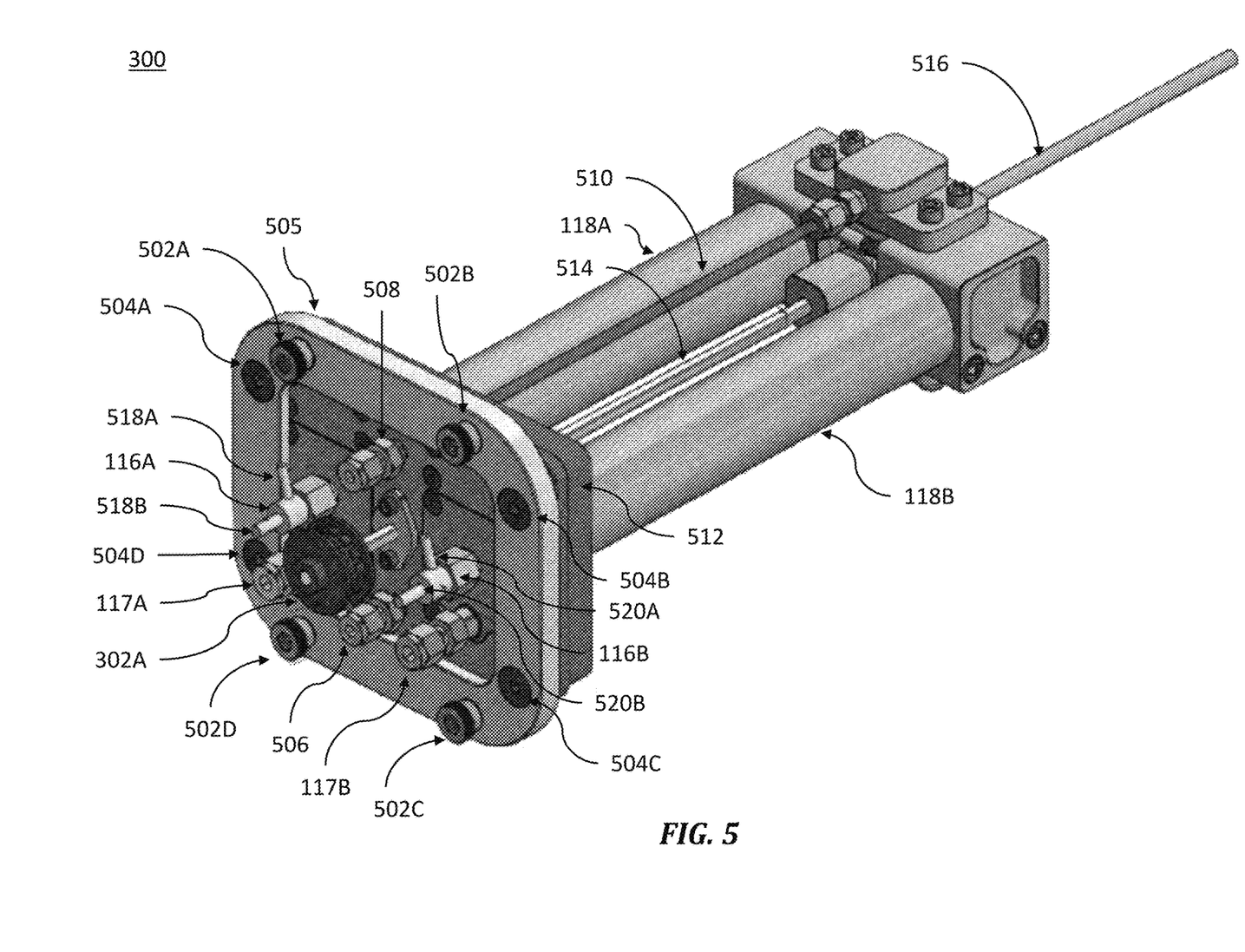
FIG. 5 is a perspective view of a removable manifold assembly according to one embodiment.
Figure 6A:
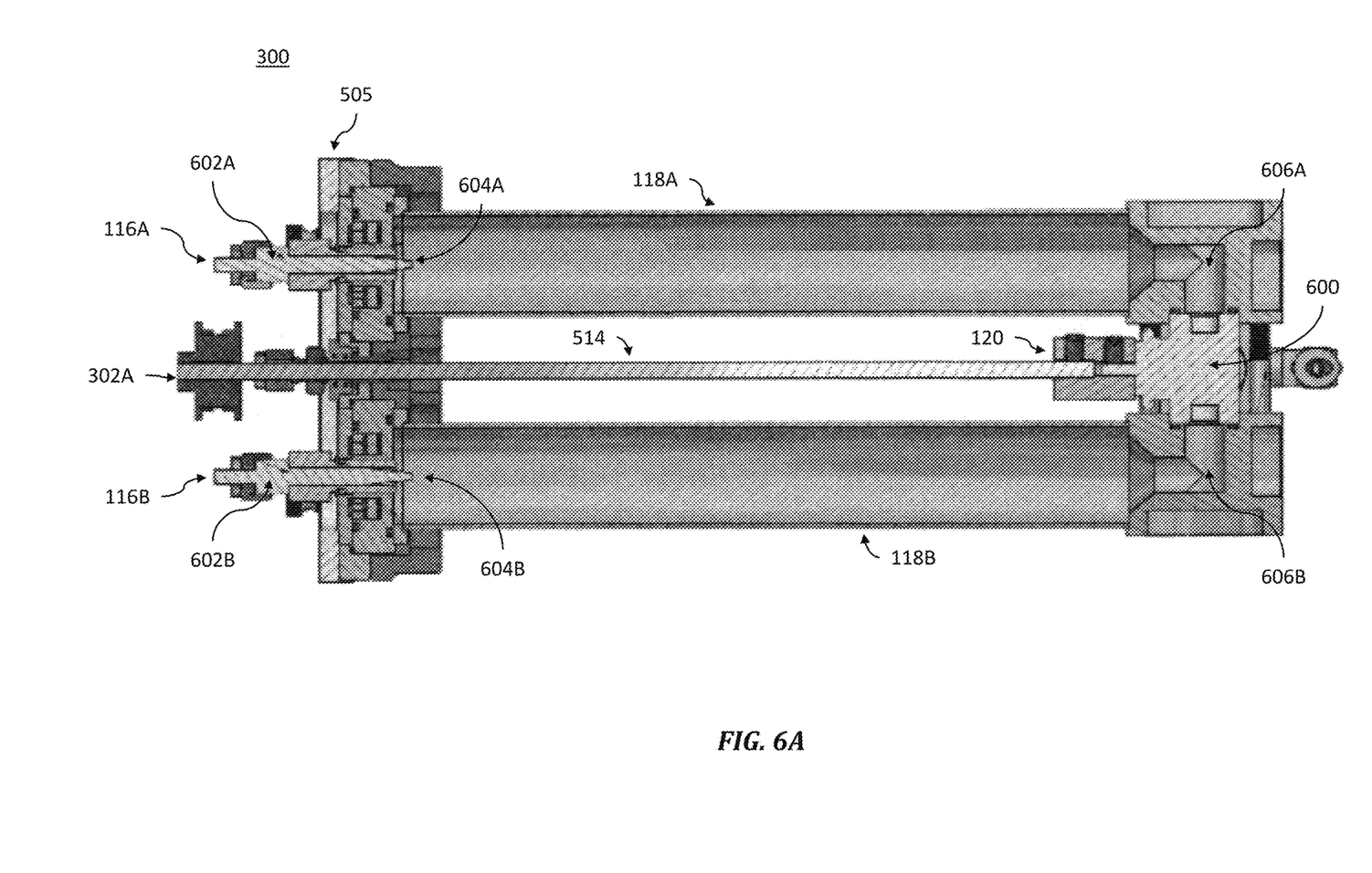
FIG. 6A is a top-down cross-sectional view of the removable manifold assembly according to one embodiment.
Figure 6B:
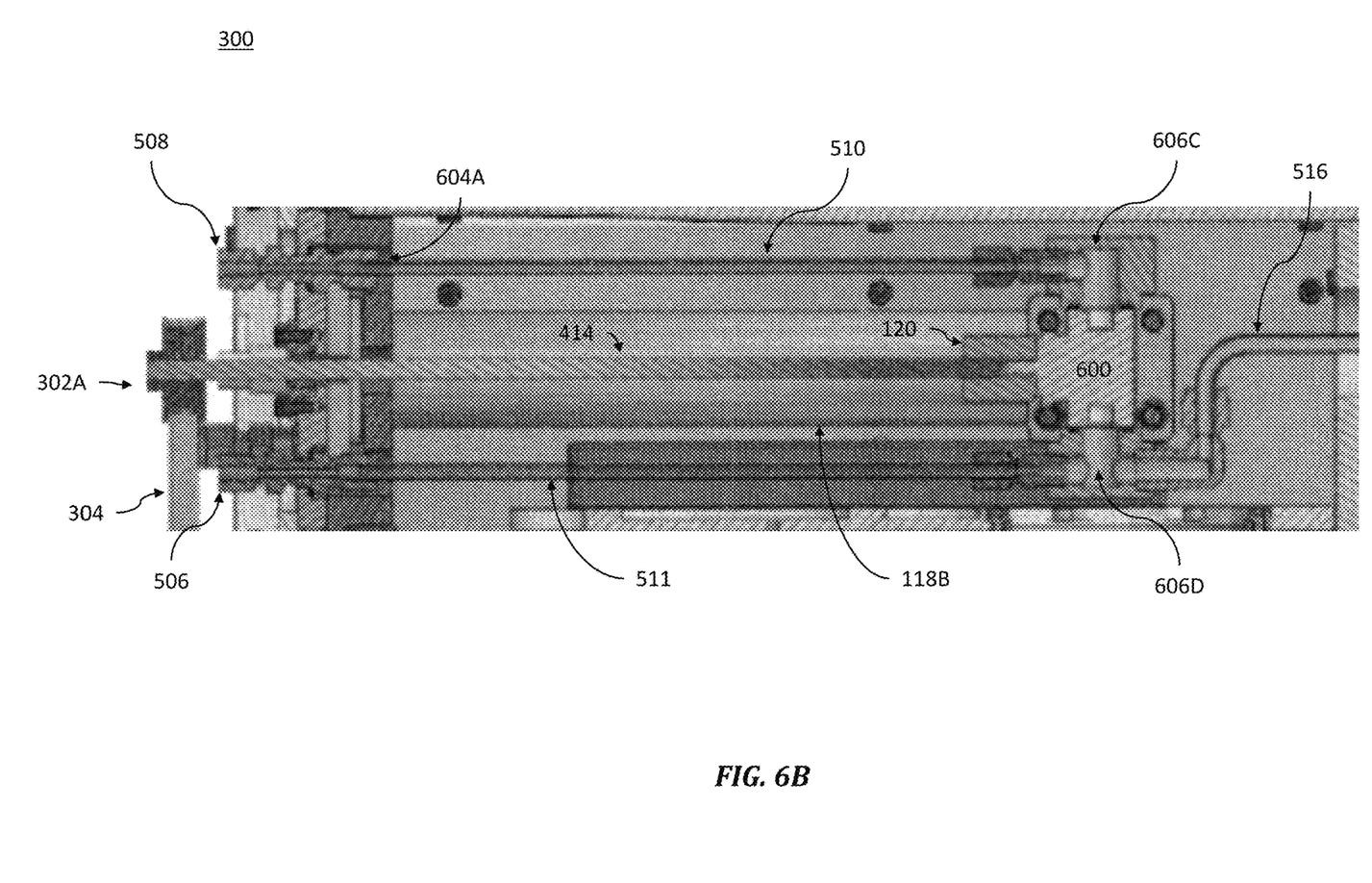
FIG. 6B is a side cross-sectional view of the removable manifold assembly according to one embodiment.
Figure 7A:
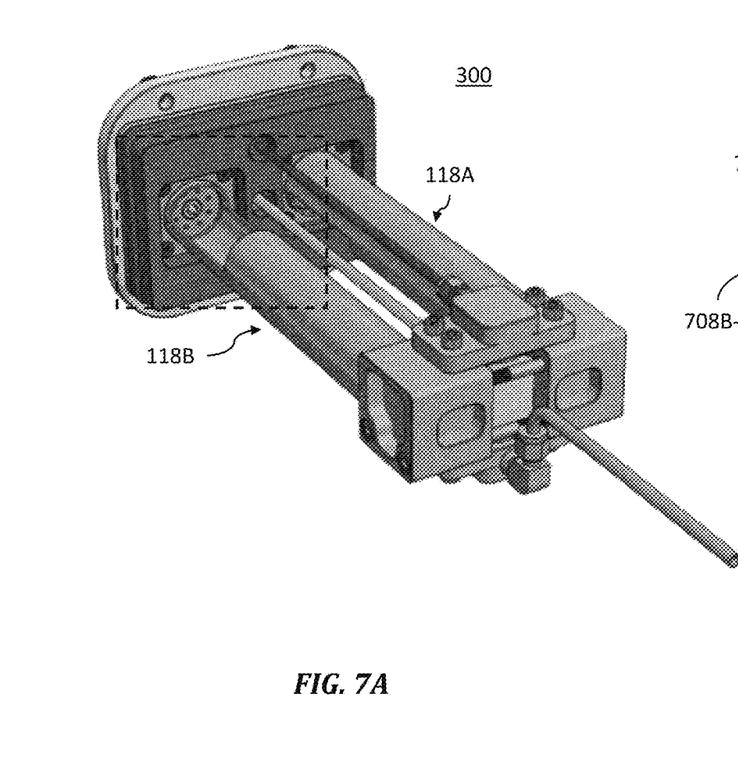
FIG. 7A is a perspective view of the removable manifold assembly.
Figure 7B:
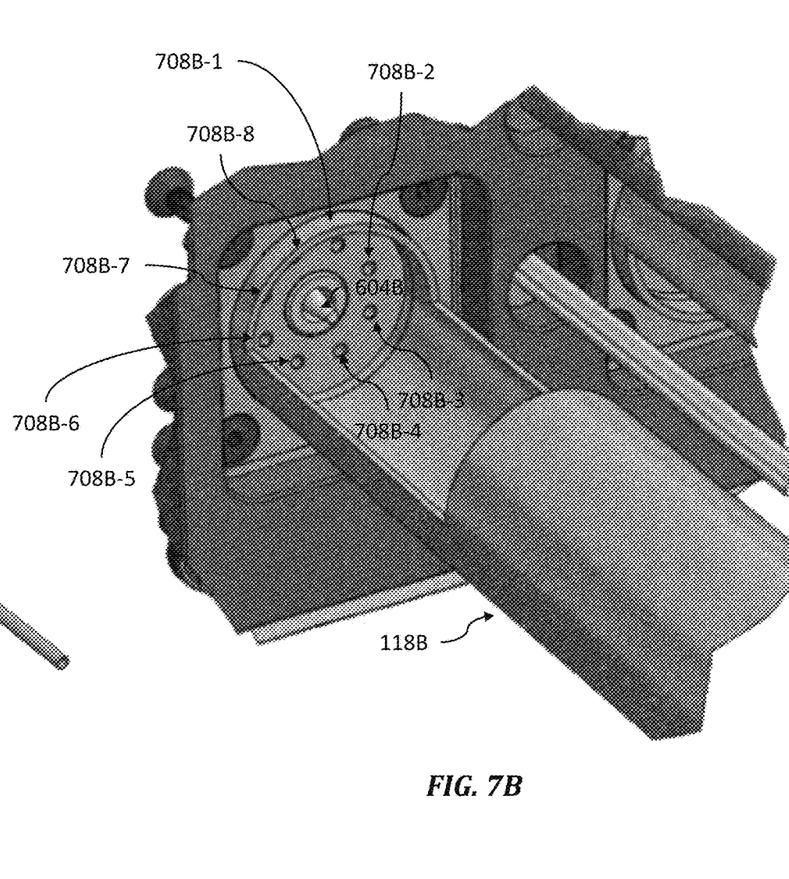
FIG. 7B is an enlarged perspective view of a portion of the removable manifold assembly shown in FIG. 7A.
Figure 7C:
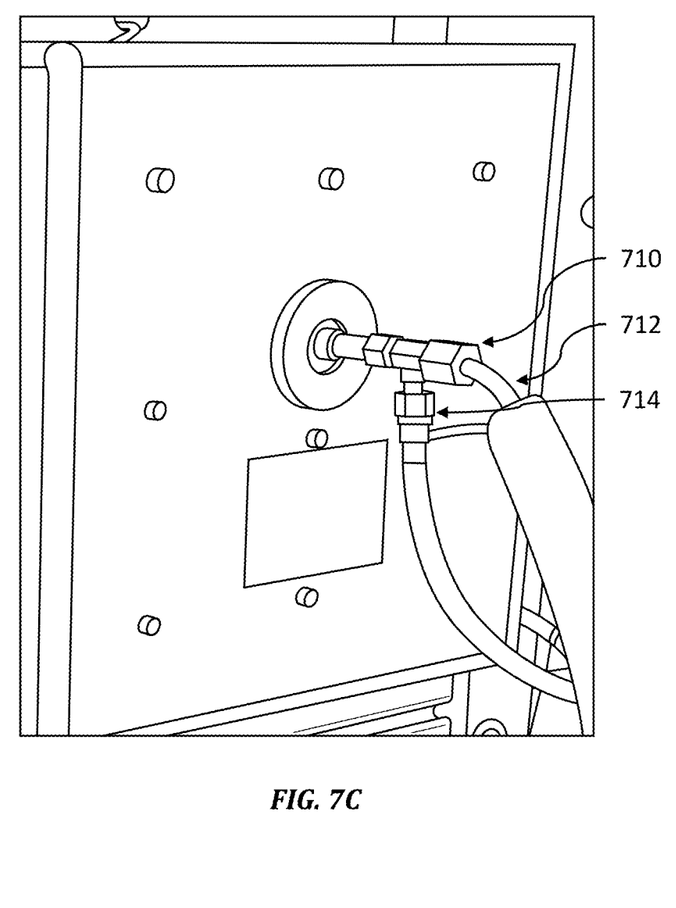
FIG. 7C is a perspective view of the rear of oven 100B showing a t-fitting connecting an output port to an exhaust hood and a sensor.
Figure 8A:
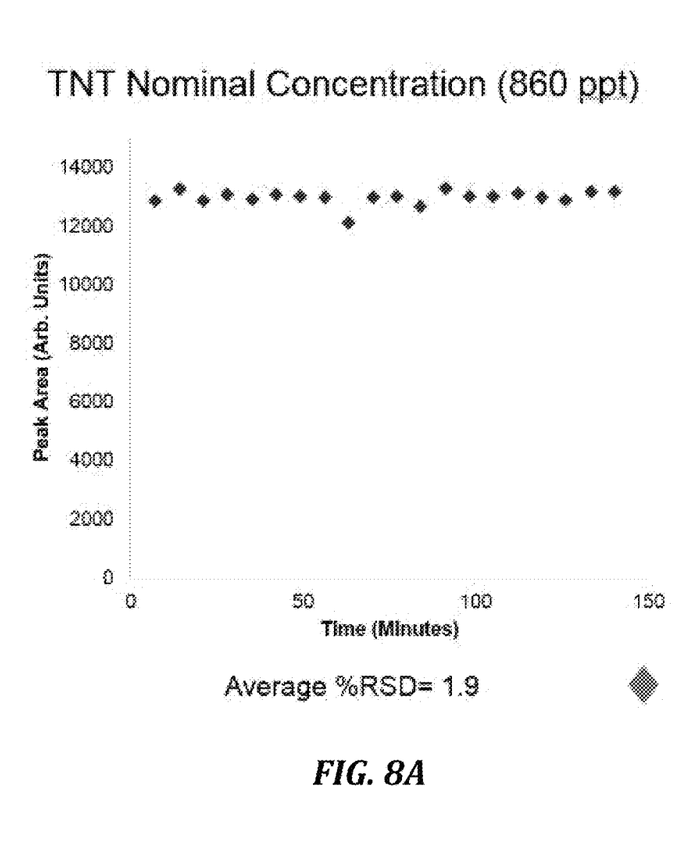
FIGS. 8A and 8B are graphs illustrating the performance of the trace vapor generator according to one embodiment.
Figure 8B:
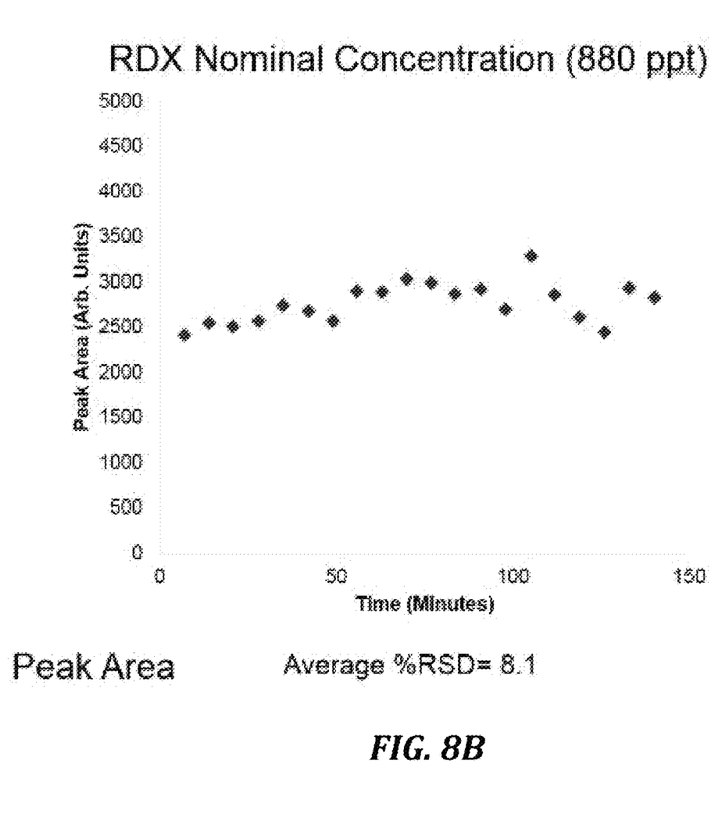
Figure 9A:
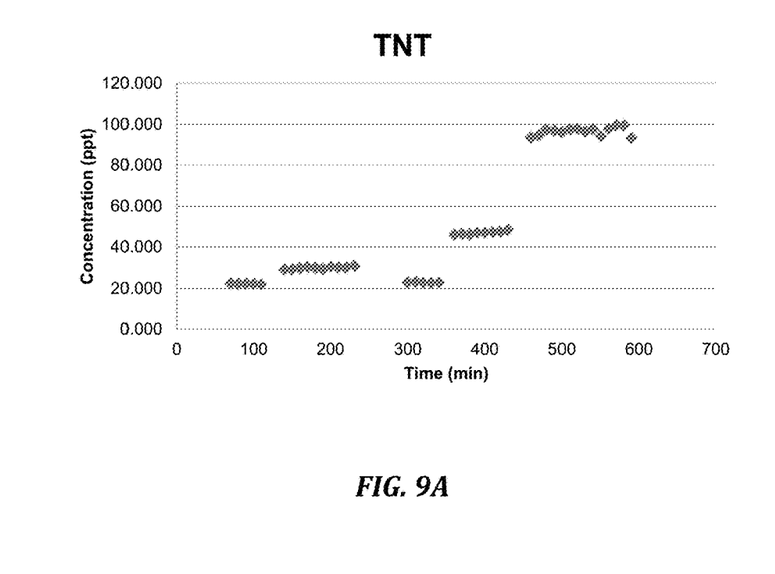
FIGS. 9A and 9B are additional graphs illustrating the performance of the trace vapor generator according to one embodiment.
Figure 9B:
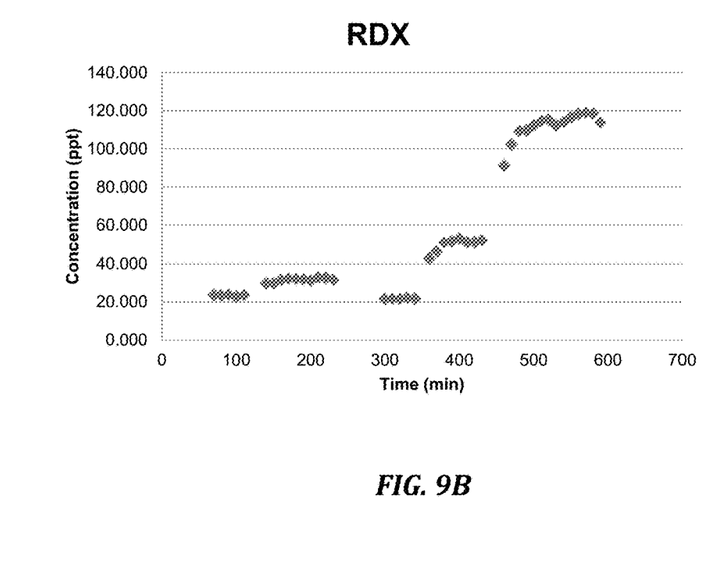

FIG. 5 is a perspective view of the removable manifold assembly 300, according to one embodiment. FIG. 6A is a side cross-sectional view of the removable manifold assembly 300, according to one embodiment. FIG. 6B is top-down cross-sectional view of the removable manifold assembly 300, according to one embodiment. As shown in FIG. 5, the exterior facing portion of the removable manifold assembly 300 is a metal flange 505 that is secured to frame 410 by a plurality of screws 502A-D. Screws 502A-D may be used in conjunction with toggles 312A-312D or in lieu thereof. In a preferred embodiment, screws 502A-D are thumbscrews that allow for tool-less access to the removable manifold assembly 300. Screws 504A-D are also provided and used to secure the exterior facing metal flange 505 to a ceramic insulation layer 512 which prevents heat loss through the metal flange 505 to the exterior. Protruding from flange 505 are the carrier gas inlets 117A and 117B. Also provided, are exhaust ports 506 and 508. Port 508 is connected by a bypass line 510 to the crossover valve 600 via a connecting piece 606C. As discussed above, crossover valve 600 is operated by a drive shaft 514 that connects crossover valve 600 to pulley 302A; thus establishing an operable path from the pneumatic actuator 306 to the crossover valve 600. Exhaust port 506 is connected to exhaust line 511, which attaches by connection piece 606D to both the crossover valve 600 and to port 134 by line 516.

Finally, distal portions, that is away from the interior of oven 100B, of nebulizers 116A and 116B protrude through the flange 505. These distal portions include connections for receiving liquid and gas from controller 100A. More specifically, nebulizer 116A includes a liquid supply connection 518B for receiving the flow of clean solution 124A from liquid supply port 110A, and a carrier gas connection 518A for receiving carrier gas flow 126A. In a similar manner, nebulizer 116B includes a liquid supply connection 520B for receiving the flow of analyte solution 124B from liquid supply port 110B, and a carrier gas connection 520A for receiving carrier gas flow 128A.

FIG. 6A shows that the proximate portions of nebulizers 116A and 116B, that is the portions of nebulizers 116A and 116B that are closer to the interior of oven 100B and beyond flange 505. By controlling the volume of liquid in the flow of clean solution 124A and the amount of gas in the carrier gas flow 126A, a gaseous vapor with a precise concentration can be generated and emitted from nebulizer 116A through nozzle 604A. In a similar manner, the flows of analyte solution 124B and carrier gas 128A are mixed in nozzle chamber 602B of nebulizer 116B. Again, by controlling the volume of liquid in the flow of analyte solution 124B and the amount of gas in the carrier gas flow 128A, a gaseous vapor with a precise concentration can be generated and emitted from nebulizer 116B through nozzle 604B. Nozzles 604A and 604B eject their respective gaseous vapors into manifolds 118A and 118B, respectively. In addition to the gaseous vapors ejected by nozzles 604A and 604B into manifolds 118A and 118B, respectively, sheath flows of the carrier gas are also generated in each manifold, as explained below in reference to FIGS. 7A and 7B.

FIG. 7A is another perspective view of the removable manifold assembly 300. In FIG. 7A, a portion of manifold 118B has been removed to illustrate the interior thereof. The same configuration is also present in the interior of manifold 118A, and thus illustration thereof has been omitted due to its duplicative nature. FIG. 7B is a close-up view of a portion of FIG. 7A denoted by the dashed-line box. As shown in FIGS. 7A and 7B, manifolds 118A and 118B include respective sheath flow inlets 708$A_i$ and 708$B_i$. In the embodiment shown in FIG. 7B there are eight sheath flow inlets for each manifold: 708A-1 . . . 708A-8 for manifold 118A and 708B-1 . . . 708B-8 for manifold 118B. However, two, four, six, or ten inlets may also be used for each manifold. Sheath inlets 708A-1 . . . 708A-8 are connected to carrier gas inlet 117A and receive and discharge carrier gas from flow 126B. Sheath inlets 708B-1 . . . 708B-8 are connected to carrier gas inlet 117B and receive and discharge carrier gas from flow 128B. As shown in FIG. 7B, in one embodiment the sheath inlets 708$A_i$ and 708$B_i$ are disposed in a circular arrangement and surround nozzles 604A and 604B of nebulizers 116A and 116B, respectively. Thus, the gaseous vapor emitted by nebulizers 116A and 116B is further combined with sheath flows from sheath inlets 708$A_i$ and 708$B_i$ in manifolds 118A and 118B. Mixing the nebulizer carrier gas with the sheath gaseous vapor is an effective way of 1) transporting low vapor pressure explosives compounds that have a tendency to adsorb onto surfaces, and 2) further controlling the analyte concentration through dilution and mixing. In a preferred embodiment, processor 104 is configured to control flows 124A, 124B, 126A, 126B, 128A, and 128B such that the humidity vapor concentrations in manifolds 118A and 118B are substantially equal. As discussed above, heater 126 heats the oven 100B and in turn manifolds 118A and 118B to a sufficient temperature to prevent adsorption of the vapor onto the surfaces of manifolds 118A and 118B. In addition, air heated by heater 126 contacts the metal flange 505, which contains the sheath inlets 708$A_i$ and 708$B_i$, thereby warming the metal flange 505 and in turn the sheath inlets 708$A_i$ and 708$B_i$. Heating the sheath inlets 708$A_i$ and 708$B_i$ enables the carrier gas for the sheath flow to be brought to an elevated temperature. In one preferred embodiment, flange 505 may also direct the carrier gas through an ever increasing number of flow paths. For example, the carrier gas may move from two to four to eight evenly distributed flow paths before emerging from inlets 708$A_i$ and 708$B_i$. This design promotes effective warming of the inlet carrier gas, promoting the evaporation of the liquid droplets emanating from the nebulizers as they traverse the manifolds.

Manifolds 118A and 118B are connected to the crossover valve 600 by connecting chambers 606A and 606B, respectively. Crossover valve 600 may be, in a preferred embodiment, a Swagelok 4-way crossover valve. This configuration allows the clean and analyte vapors in manifolds 118A and 118B, to be provided to connector piece 606C or 606D by operation of valve 600. As noted above, valve 600 is operatively connected to actuator 306 which is controlled by processor 104. Processor 104 is therefore configured to control the flow of clean and analyte vapors to crossover valve 600. Crossover valve 600 is connected to a supply port 134 by tube 516. Thus, by controlling the operation of crossover valve 600, processor 104 is configured to control the output of supply port 134. Namely, processor 104 can direct a clean vapor or an analyte vapor to supply port 134. Moreover, processor 104 can switch the output of supply port 134 from a clean vapor to an analyte vapor by operation of crossover valve 600. This switchover may occur as rapidly as actuator 306 may allow. In one embodiment, processor 104 controls crossover valve 600 to direct vapor from either manifold 118A or 118B to supply port 134 and exhaust port 506. By capping exhaust port 506, the vapor sample may be delivered to a sensor attached to supply port 134 with positive pressure flow.

For lower positive pressures, a vacuum may be applied to exhaust port 506 to adjust the positive pressure applied to supply port 134. For detection systems which utilize their own sampling system, e.g. a vacuum sampler, exhaust port 506 may be sealed with a cap and a tee coupler 710 added to supply port 134; the detector is attached to one fitting 714 on the tee coupler to sample vapor from a gas stream which is delivered via the remaining fitting 712 to an exhaust hood, as shown in FIG. 7C.

One of the features of oven 100B is that manifolds 118A and 118B may be replaced by removing manifold assembly 300. Thus, if the operator desires to change the type of analyte, the manifolds 118A and 118B may be replaced with clean manifolds to ensure that no cross-contamination occurs. By operation of the components of system 100 described, vapor concentrations may range from parts per quadrillion to parts per million.

FIGS. 8A and 8B are graphs illustrating the operation of system 100 wherein the peak area represents the mass spectral, integrated response of a specific mass-to-charge peak selective to the monitored analyte. In FIG. 8A the analyte is TNT with a nominal concentration of 860 parts per trillion. As shown in FIG. 8, the relative standard deviation (RSD) after 140 min is 1.9%, showing that the system 100 is able to deliver accurate and controlled vapor concentrations over a long period of time. In FIG. 8B the analyte is RDX with a nominal concentration of 880 parts per trillion at an oven temperature of 120° C. Again, even after 140 minutes, the RSD is only 8.1% which a good result for RDX at this concentration. FIGS. 9A and 9B are also graphs illustrating the operation of the system 100. Here, the concentrations of the vapor at the supply port 134 were varied with time under the control of processor 104. As shown in FIG. 9A, the system 100 was able to move from TNT concentrations as low as 20 parts per trillion to 100 parts per trillion. Moreover, the system 100 shows excellent stability at each of those concentration levels. In a similar manner, system 100 was operated to vary the concentration of RDX as the analyte from 20 parts per trillion to 120 parts per trillion. Like with FIG. 9A, the system was able to accurately change and control the concentration of analyte with time.

While various example embodiments of the invention have been described above, it should be understood that they have been presented by way of example, and not limitation. It is apparent to persons skilled in the relevant art(s) that various changes in form and detail can be made therein. Thus, the disclosure should not be limited by any of the above described example embodiments, but should be defined only in accordance with the following claims and their equivalents.

In addition, it should be understood that the figures are presented for example purposes only. The architecture of the example embodiments presented herein is sufficiently flexible and configurable, such that it may be utilized and navigated in ways other than that shown in the accompanying figures.

Further, the purpose of the Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that the procedures recited in the claims need not be performed in the order presented.

What is claimed is:

1. An apparatus for generating a trace vapor, comprising:
   a controller; and
   an oven that includes
      a first manifold for receiving a first vapor stream comprising an analyte compound,
      a second manifold for receiving a second vapor stream comprising a non-analyte compound,
      an output supply port,
      an exhaust port, and
      a valve communicably connected to the output supply port, the first manifold, and the second manifold, and configured to switch between a first state, in which the first vapor stream in the first manifold is permitted to flow to the output supply port and the second vapor stream is permitted to flow to the exhaust port, and a second state, in which the second vapor stream is permitted to flow to the output supply port and the first vapor stream is permitted to flow to the exhaust port,
   wherein the first manifold and the second manifold are removably disposed in a side of the oven, and
   wherein the valve is constructed to switch between the first state and the second state in response to an instruction from the controller.

2. The apparatus of claim 1, further comprising:
   a heater disposed within the oven and configured to maintain a predetermined temperature within the oven that inhibits adsorption of the analyte compound onto a surface of the first manifold.

3. The apparatus of claim 2, further comprising:
   a fan disposed within the oven and configured to circulate air heated by the heater within the oven.

4. The apparatus of claim 1, further comprising:
   a first nebulizer nozzle partially disposed in a first end of the first manifold and configured to inject the first vapor stream into the first manifold.

5. The apparatus of claim 4, wherein the first manifold includes a first plurality of sheath flow inlets constructed to receive a carrier gas.

6. The apparatus of claim 5, wherein the first plurality of sheath flow inlets are disposed in the first end of the first manifold and at least partially surround the first nebulizer nozzle.

7. The apparatus of claim 6, further comprising:
   a heater disposed within the oven; and
   a metal flange removably connected to the oven, wherein the metal flange includes:
      a first plurality of paths within the metal flange that connect to the first plurality of sheath flow inlets, respectively, and
   wherein at least one surface of the metal flange is disposed within the oven and heated by the heater such that the first plurality of paths heat the carrier gas as the carrier gas flows to the first plurality of sheath flow inlets.

8. The apparatus of claim 6, wherein the first end of the first manifold is a distal end from the valve.

9. The apparatus of claim 6, further comprising:
   a second nebulizer nozzle partially disposed in a first end of the second manifold and configured to inject the second vapor stream into the second manifold.

10. The apparatus of claim 9, wherein the second manifold includes a second plurality of sheath flow inlets constructed to receive the carrier gas.

11. The apparatus of claim 10, wherein the second plurality of sheath flow inlets are disposed in the first end of the second manifold and at least partially surround the second nebulizer nozzle.

12. The apparatus of claim 11, further comprising:
   a heater disposed within the oven; and
   a metal flange removably connected to the oven, wherein the metal flange includes:
      a first plurality of paths within the metal flange that connect to the first plurality of sheath flow inlets, respectively, and
      a second plurality of paths within the metal flange that connect to the second plurality of sheath flow inlets, respectively, and
   wherein at least one surface of the metal flange is disposed within the oven and heated by the heater such that the first plurality of paths and the second plurality of paths heat the carrier gas as the carrier gas flows to the first plurality of sheath flow inlets and the second plurality of sheath flow inlets.

13. The apparatus of claim 11, wherein the first end of the second manifold is a distal end from the valve.

* * * * *